US012639835B2

(12) United States Patent       (10) Patent No.: US 12,639,835 B2

Plishker et al.                     (45) Date of Patent:       May 26, 2026

(54) METHOD AND APPARATUS OF FUSION OF MULTIMODAL IMAGES TO FLUOROSCOPIC IMAGES

(71) Applicant: ACREW Imaging, Inc., Ocean View, DE (US)

(72) Inventors: William Plishker, Ocean View, DE (US); Craig Hughes, Ocean View, DE (US)

(73) Assignee: ACREW IMAGING, INC., Ocean View, DE (US)

( * ) Notice: Subject to any disclaimer, the term of this patent is extended or adjusted under 35 U.S.C. 154(b) by 283 days.

(21) Appl. No.: 18/254,733

(22) PCT Filed: Dec. 2, 2021

(86) PCT No.: PCT/US2021/061560

§ 371 (c)(1),
(2) Date: May 26, 2023

(87) PCT Pub. No.: WO2022/120018

PCT Pub. Date: Jun. 9, 2022

(65) Prior Publication Data

US 2024/0020860 A1      Jan. 18, 2024

Related U.S. Application Data

(60) Provisional application No. 63/120,476, filed on Dec. 2, 2020.

(51) Int. Cl.
*G06T 7/33*       (2017.01)
*G06T 5/50*       (2006.01)
(Continued)

(52) U.S. Cl.
CPC .............. *G06T 7/337* (2017.01); *G06T 5/50* (2013.01); *G06T 7/37* (2017.01); *G06T 7/38* (2017.01);
(Continued)

(58) Field of Classification Search
CPC .. G06T 7/337; G06T 5/50; G06T 7/37; G06T 7/38; G06T 2200/24; G06T 2207/10016;
(Continued)

(56) References Cited

U.S. PATENT DOCUMENTS 6,837,892 B2    1/2005 Shoham
9,135,706 B2 *  9/2015 Zagorchev ............. A61B 6/487
(Continued)

FOREIGN PATENT DOCUMENTS

CN      110148160  A     8/2019
JP      2015-518383 A    7/2015
(Continued)

OTHER PUBLICATIONS

Haque, Md Nazmul, et al. "A fast and robust technique for 3D-2D registration of CT to single plane X-ray fluoroscopy." Computer Methods in Biomechanics and Biomedical Engineering: Imaging & Visualization 2.2 (2014): 76-89. (Year: 2014).*
(Continued)

*Primary Examiner* — Henok Shiferaw
*Assistant Examiner* — Dion J Satcher
(74) *Attorney, Agent, or Firm* — Edwards Neils LLC; Jean C. Edwards, Esq.

(57)                     ABSTRACT

The present invention includes a device for transforming 3D image data such that the transformed image aligns with a 2D fluoroscopic image. The process of finding the transform that aligns the features of the 3D image with the 2D image is called image registration. The fluoroscopic image registration process has at its core a multistage framework that (Continued)

progressively refines a registration result. Each stage leverages the fluoroscopic registration engine which iteratively searches the parameter space defined by the stage. The core registration engine creates a candidate transform, uses it to create a digitally reconstructed radiograph, then compares that to the supplied fluoroscopic image, and the iterative alignment engine either ends or uses it to construct a new candidate transform. Similarity measurement of a candidate transform is based on intensities and any custom data relevant to the registration scenario.

17 Claims, 8 Drawing Sheets

(51) Int. Cl.
| | | |
|---|---|---|
| *G06T 7/37* | (2017.01) | |
| *G06T 7/38* | (2017.01) | |
| *G16H 30/20* | (2018.01) | |

(52) U.S. Cl.
CPC ......... *G16H 30/20* (2018.01); *G06T 2200/24* (2013.01); *G06T 2207/10016* (2013.01); *G06T 2207/10121* (2013.01); *G06T 2207/10124* (2013.01); *G06T 2207/20221* (2013.01); *G06T 2207/30004* (2013.01)

(58) Field of Classification Search
CPC . G06T 2207/10121; G06T 2207/10124; G06T 2207/20221; G06T 2207/30004; G06T 2207/30096; G06T 2207/30101; G06T 7/223; G06T 7/248; G06T 7/35; G06T 7/0014; G16H 30/20; A61B 2090/376; A61B 6/481; A61B 6/504; A61B 6/5223; G06V 10/80; G06V 20/69
USPC ......................................................... 382/254
See application file for complete search history.

(56) References Cited

U.S. PATENT DOCUMENTS

| | | | | |
|---|---|---|---|---|
| 2007/0110289 | A1* | 5/2007 | Fu ......................... | G06V 10/24 |
| | | | | 382/128 |
| 2007/0237370 | A1 | 10/2007 | Zhou et al. | |
| 2011/0152676 | A1* | 6/2011 | Groszmann .............. | A61B 6/12 |
| | | | | 600/426 |
| 2012/0027261 | A1 | 2/2012 | Frank et al. | |
| 2012/0296202 | A1 | 11/2012 | Mountney et al. | |
| 2013/0070995 | A1 | 3/2013 | Chou et al. | |
| 2013/0094745 | A1 | 4/2013 | Sundar | |
| 2013/0177230 | A1 | 7/2013 | Feng et al. | |
| 2014/0334709 | A1* | 11/2014 | Siewerdsen .............. | G06T 7/32 |
| | | | | 382/132 |
| 2015/0015582 | A1 | 1/2015 | Kaiser et al. | |
| 2015/0043798 | A1 | 2/2015 | Carrell et al. | |
| 2016/0242724 | A1* | 8/2016 | Lavallee ................ | A61B 6/032 |
| 2017/0024634 | A1* | 1/2017 | Miao ........................ | G06N 3/04 |
| 2017/0337682 | A1* | 11/2017 | Liao .......................... | G06T 7/30 |
| 2019/0133693 | A1* | 5/2019 | Mahfouz .................. | A61B 6/12 |
| 2020/0107884 | A1* | 4/2020 | Razeto ................... | A61B 6/032 |
| 2020/0405399 | A1* | 12/2020 | Steinberg .............. | A61B 90/50 |
| 2021/0386480 | A1* | 12/2021 | Tolkowsky ............ | A61B 46/20 |

FOREIGN PATENT DOCUMENTS

| | | |
|---|---|---|
| JP | 5950782 B2 | 7/2016 |
| WO | 2015/175848 A1 | 11/2015 |

OTHER PUBLICATIONS

International Search Report issued in PCT/US2021/061560 on Feb. 18, 2022.
Written Opinion issued in PCT/US2021/061560 on Feb. 18, 2022.
International Preliminary Report on Patentability issued by WIPO on May 30, 2023, in connection with International Patent Application No. PCT/JP2021/061560.
Office Action, which was issued by the Saudi Authority for Intellectual Property on Mar. 20, 2024, in connection with Saudi Arabian Patent Application No. 523440996.
Extended European Search Report issued by the European Patent Office on Oct. 10, 2024, in connection with European Patent Application No. 21901445.3.
Lyubomir Zagorchev et al, Rapid fusion of 2D X-ray fluoroscopy with 3D multislice CT for image-guided electrophysiology procedures, Proceedings of SPIE, Jan. 1, 2007, p. 65092B, vol. 6509, Visual communications and image processing 2005, Beijing, China.
Haque M.N. et al, A slice based technique for low-complexity 3D/2D registration of CT to single plane X-ray fluoroscopy, Digital Image Computing Techniques and Applications (DICTA), 2012 International Conference on IEEE, Dec. 3, 2012, pp. 1-6.
U. Von Jan et al, Computer Assisted Orthopaedic Surgery, International Journal of Computer Assisted Radiology and Surgery, Jun. 1, 2006, vol. 1, No. 7, pp. 229-250, Berlin, DE.
Office Action, issued by the Japanese Patent Office on Sep. 30, 2025, in connection with Japanese Patent Application No. 2023-534352.

* cited by examiner

METHOD AND APPARATUS OF FUSION OF MULTIMODAL IMAGES TO FLUOROSCOPIC IMAGES

CROSS-REFERENCE TO RELATED APPLICATIONS

The present application is a 35 U.S.C. 371 National Stage Entry of PCT/US2021/061560, filed on Dec. 2, 2021, which claims the benefit of priority from U.S. Provisional Patent Application No. 63/120,476 filed Dec. 2, 2020, the contents of all of which are incorporated herein by reference in their entirety.

BACKGROUND OF THE INVENTION

1. Field of the Invention

The present invention relates to novel image fusion of three-dimensional (3D) diagnostic images with navigational two-dimensional (2D) images, including for example, 2D x-ray images. More particularly, the invention relates to a device and a method that is capable of correcting and fusing previously acquired 3D images and combining them with contemporaneously obtained (live/real-time) 2D images from a device that produces 2D images such as an x-ray fluoroscopic system.

2. Description of the Related Art

Fluoroscopy is an imaging technique that uses X-rays to obtain real-time dynamic (moving) images of the interior of an object such as the human body. In its primary application in medical imaging, a fluoroscope allows a physician to see the internal structure and function of a patient, so that the pumping action of the heart or the motion of swallowing, for example, can be observed. This is useful for both diagnosis and therapy and has been applied in general radiology, radiation oncology, interventional radiology, interventional cardiology, surgery, particularly image guided surgery, and other areas of medicine.

In one of its simplest forms, a fluoroscope includes an X-ray source and an image intensifier/detector between which a patient is placed. Most fluoroscopes have included X-ray image intensifiers and cameras as well, to improve the visibility of the image and make it available on a local or remote display screen.

For many decades, fluoroscopy tended to produce live pictures that were not recorded, but since the 1960s, as technology improved, recording of specific portions of an examination and playback became the norm.

Fluoroscopy has a number of limitations that prevent it from being more useful to clinicians. First, because it utilizes ionizing radiation, every moment the fluoroscope is on creates additional radiation risk to patients and others in the room. The consensus of experts, and numerous studies link increased radiation exposure to increased cancer rates and direct or indirect tissue damage. In practice, these effects limit the amount of radiation a patient may be exposed to, which in turn, limits the number of fluoroscopic images that may be taken in a period of time, and limits the quality of those images.

Secondly, unlike computed tomography (CT) and magnetic resonance imaging (MRI), x-ray fluoroscopy has limited sensitivity to certain structures in the body. For example, while bones are almost always visible, soft tissue structures are often much less so. Some structures such as vessels can be readily seen when they are injected with a contrast media, which is a liquid that creates additional density; hence, contrast in the fluoroscopic image. For vascular interventions, contrast agents are typically iodine based, which can result in some toxicity to the kidneys.

These limitations cause physicians at times to limit their own visualization of a procedure, potentially the time required to perform them. This can also expose patients who are sedated to the additional risks associated with awake sedation/anesthesia. For patients under general anesthesia, longer procedure times are correlated with longer hospital stays and lengthier recovery. More generally, a limitation on visualization is likely to lead to poorer outcomes with real-time navigational decisions being impaired by the lack of meaningful anatomical information provided at that moment.

Therefore, a need exists in the field for novel visualization solutions, capable of delivering meaningful image information in an accurate and timely fashion. Some approaches are already addressing some aspects of the problem. For example, digitally reconstructed radiographs (DRRs) simulate a fluoroscopic image from a 3-dimensional computed tomography (CT) image. Tracking hardware can be used to determine the parameters needed to construct a DRR that accurately overlays with a fluoroscopic engine.

While these and other aspects of the solution exist, there does not exist a fiducial-free (or "markerless") tracking solution that can uncover the transformational parameters needed to create an enhanced DRR that overlays structures from 3D images such as CT, MRI and positron emission tomography (PET) scans onto fluoroscopic images in a generalized way throughout the entire human body.

SUMMARY OF THE INVENTION

The present invention relates to novel image fusion of three-dimensional (3D) diagnostic images with navigational two-dimensional (2D) projection images, including for example, 2D x-ray images. More particularly, the invention relates to a device and a method that is capable of correcting and fusing previously acquired 3D images and combining them with contemporaneously obtained (live/real-time) 2D images from a device that produces 2D images such as an x-ray fluoroscopic system. This allows a structure such as the abdominal aorta which might be invisible on a conventional 2D fluoroscopic image to be easily seen and dynamically tracked due to an overlay of that aorta from a CT, MRI, 3D or volumetric ultrasound or other cross sectional/3D imaging scan.

In one embodiment, the present invention includes a device for transforming a 3D image data set such that the transformed image aligns with a 2D fluoroscopic image data set. The process of the present invention, in finding the transform that aligns the features of the 3D image with the 2D image is deemed "image registration" by the inventors.

In one embodiment, the present invention relates to multiple stages of finding an optimal set of transformational parameters to drive a match of a digitally reconstructed radiograph (DRR) with the fluoroscopic image, which is called "fluoroscopic image registration" by the inventors.

More specifically, the fluoroscopic image registration system of the present invention has at its core a multistage framework that progressively refines an image registration result. In one embodiment, each stage leverages the same core registration engine or module which iteratively searches the parameter space defined by the stage. In one embodiment, the core registration engine creates a candidate transform, uses it to create the DRR, then compares that to the supplied fluoroscopic image, and then either ends, or uses it to construct a new candidate transform. In one embodiment, similarity measurement of a candidate transform is based on intensities and any custom data relevant to the registration scenario.

Generally speaking, in one embodiment, the algorithm of the present invention begins in the first stage by the core registration engine using starting parameters (i.e., images and any previously transformed images) defined by the user position initialization (e.g., anteroposterior (AP) abdomen) and using it to construct a candidate DRR ("candidate transformation parameters"). However, many of the functions to achieve the same results are contributed by the event classifier of the iterative alignment engine.

In one embodiment, the similarity of the DRR and actual fluoroscopic image is recorded in memory by the core registration engine, and image volume, image frame, and candidate transform are transferred to the iterative alignment engine, and the algorithm proceeds iteratively with a perturbed candidate transform in the second stage as controlled by the iterative alignment engine ("digital radiograph reconstruction".

In one embodiment, the resulting similarities determined by the iterative alignment engine (third stage, "similarity"), continue to be recorded with an optimization engine of the core registration engine, the optimization engine which, in the fourth stage, guides the creation of new candidate transforms from these results ("optimization engine"), which are in turn used to generate a DRR image which is then assessed for a match with the latest fluoroscopic navigational image.

In one embodiment, in the event that the transformation is not acceptable based on predetermined parameters by the iterative alignment engine, a new candidate transform is created by the iterative alignment engine. Iterations continue as controlled by the iterative alignment engine, until a convergence criterion is reached, and the best candidate transform is applied to a structure of interest in the volumetric space and the result blended with the original fluoroscopic frame.

In one embodiment, an image registration system, includes: a fluoroscopic registration engine which iteratively refines a digitally reconstructed radiograph (DRR) image from a PACS imaging source, with a fluoroscopic image from a fluoroscopic imaging equipment source, to match the DRR image with the fluoroscopic image, the fluoroscopic registration engine being disposed at one of a client computer or a server, the fluoroscopic registration engine including: a core registration module which creates a candidate transform to achieve the DRR image, and compares the DRR image to the fluoroscopic image; a graphics memory module including: a volume data storage that stores volume data from the PACS imaging source; a video data storage that stores video data from the fluoroscopic imaging source; wherein the core registration module controls acquisition of the data from the PACS imaging source and the fluoroscopic imaging equipment source, and transmission and storage of the data to the graphics memory module; and an iterative alignment module which assesses the DRR image for a match with the fluoroscopic image, and proceeds iteratively with a new candidate transform from the core registration module to generate a new DRR image until a match with the new DRR image is achieved, and the new candidate transform is applied to a structure in a volumetric space and blended with the fluoroscopic image to result in a transformed image and accomplish image registration.

In one embodiment, the image registration system further includes: an input memory module which receives and stores data from the PACS imaging source and the fluoroscopic imaging equipment source prior to transmission of the data to the graphics memory module, the input memory module including: a volume data storage that stores volume data from the PACS imaging source; and a video data storage that stores video data from the fluoroscopic imaging equipment source.

In one embodiment, the image registration system further includes: a frame grabber module connected to the fluoroscopic imaging equipment source, the frame grabber module which captures individual digital frames from a stream of the video data from the fluoroscopic imaging equipment source, and transmits the video data to the video data storage of the input memory module.

In one embodiment, the core registration module further includes: an event classifier which autonomously determines a status of the image registration; wherein the event classifier takes as inputs a plurality of fluoroscopic image frames grabbed from the fluoroscopic imaging equipment source by the frame grabber module, such that the core registration module examines properties of a current fluoroscopic image frame of the plurality of fluoroscopic image frames to compare with the DRR image to ascertain the match and to dynamically invoke the image registration.

In one embodiment, the image registration system further includes: a display of a computer system; and wherein the core registration module further includes: a graphical user interface (GUI) module that supports loading, viewing and interaction of fluoroscopic images received from the input memory module, and allows a user to interact with the fluoroscopic registration engine and display at least one of said fluoroscopic images and the transformed image on said display screen.

In one embodiment, the graphics memory module further includes: an output frame buffer module which receives the transformed image from the iterative alignment module and transfers the transformed image to the display as a rendered image.

In one embodiment, the iterative alignment module further includes: a candidate transform module which uses starting parameters of the DRR image and any previously transformed DRR images to construct the new candidate transform; a digital reconstruction module which takes the new candidate transform and generates the new DRR image; and a similarity module which determines similarities between the new DRR image and the fluoroscopic image to determine the match.

In one embodiment, the core registration module further includes: an optimization module which guides a creation of the new candidate transform of the candidate transform module from results of similarities found by the similarity module.

In one embodiment, the core registration module performs 3-parameter registration which represent a 2D rigid transform on the new DRR image.

In one embodiment, the core registration module performs 6-parameter registration after the 3-parameter registration, to account for out-of-plane rotations and any variation in distance of a patient body from the fluoroscopic imaging equipment.

In one embodiment, nonrigid registration is performed on the new DRR image to account for nonlinear motion of structures, where each parameter of a multi-parameter nonrigid registration can model a local deformation in the new DRR image.

In one embodiment, a method of performing image registration, including: launching an image registration session on a display of a computer system utilizing a graphics user interface (GUI) module, the GUI module which provides an interface for a user and a fluoroscopic image registration system; initiating a fluoroscopic registration engine of the fluoroscopic image registration system, the fluoroscopic registration engine being disposed at one of a client computer or a server; wherein the fluoroscopic image registration engine performs the following steps: creating a candidate transform using a core registration module of the fluoroscopic registration engine to achieve a digitally reconstructed radiograph (DRR) image; comparing the DRR image to the fluoroscopic image using an iterative alignment module of the fluoroscopic registration engine; assessing the DRR image for a match with the fluoroscopic image; iteratively refining the DRR image with a new candidate transform from the core registration module to generate a new DRR image until a match with the new DRR image is achieved; applying the new candidate transform which achieves the match, to a structure in a volumetric space; and blending the new candidate transform with the fluoroscopic image to result in a transformed image and image registration.

In one embodiment, the core registration module controls acquisition of said data from the PACS imaging source and the fluoroscopic imaging equipment source, and transmission and storage of the data to the graphics memory module.

In one embodiment, the method of performing image registration further includes: capturing individual digital frames from a stream of video data from the fluoroscopic imaging equipment source using a frame grabber module connected to the fluoroscopic imaging equipment source; and transmitting the video data to a video data storage of an input memory module of the fluoroscopic registration engine.

In one embodiment, the method of performing image registration further includes: autonomously determining a status of the image registration using an event classifier of the iterative alignment engine module; wherein the event classifier takes as inputs a plurality of fluoroscopic image frames grabbed from the fluoroscopic imaging equipment source by the frame grabber, such that the core registration module examines properties of a current fluoroscopic image frame of the plurality of fluoroscopic image frames to compare with the DRR image for the match and to dynamically invoke the image registration.

In one embodiment, the method of performing image registration further includes: providing a display on which at least one of the fluoroscopic images received from the input memory module, and the transformed image received from an output frame buffer module, are displayed such that the user can load, view, and interact with the fluoroscopic images; wherein the output frame buffer module receives the transformed image from the iterative alignment module and transfers the transformed image to the display as a rendered image.

In one embodiment, the method of performing image registration further includes: constructing the new candidate transform using a candidate transform module of said iterative alignment module, by using starting parameters of the DRR image and any previously transformed DRR images to construct the new candidate transform; generating the new DRR image using a digital reconstruction module of the iterative alignment engine; and determining similarities between the new DRR image and the fluoroscopic image to determine the match, using a similarities module of the iterative alignment engine.

In one embodiment, the method of performing image registration further includes: creating the new candidate transform of the candidate transform module using an optimization module of the core registration module, from results of the similarities determined by the similarity module.

In one embodiment, the method of performing image registration further includes: performing 3-parameter registration using the core registration module, which represents a 2D rigid transform on the new DRR image; and performing 6-parameter registration after the 3-parameter registration using the core registration module, to account for out-of-plane rotations and any variation in distance of a patient body from the fluoroscopic imaging equipment.

In one embodiment, the method of performing image registration further includes: performing nonrigid registration on the new DRR image to account for nonlinear motion of structures, where each parameter of a multi-parameter nonrigid registration can model a local deformation in the new DRR image.

In one embodiment, the fluoroscopic registration engine enables a unique method for labeling and indexing fluoroscopic video data, where the core registration engine takes the video capture described above with respect to exemplary workflows, and any other annotations created by 3D imaging data (i.e., labels automatically annotated based on registration and pre-existing atlas), and associates the annotation with a set of pixels in each video frame, if present.

In one embodiment, another use case would be semantic indexing of an interventional procedure using the core registration engine of the fluoroscopic registration engine such that the most important/clinically relevant portions of a procedure can be reviewed, such as stent insertion, or needle biopsy or ablation or contract injection, etc.

In one embodiment, the fluoroscopic registration engine enables fluoroscopic motion stabilization through target tracking where the fluoroscopic stabilization of the present invention fixes a certain object in the same location in a video stream even if it is moving in the raw video feed. This method would also apply in radiation therapy where patient motion is tracked using the fluoroscopic registration engine, and fed back to the treatment delivery system as updated tracking information of actual movement of the tumor. In one embodiment, the target motion is used to guide the radiation beam used to treat the patient, the radiation beam moving along with the tumor, or alternatively, the radiation beam can be modulated or only turned on when the tumor is located within a certain region to maximize the accuracy of the treatment despite patient/tumor motion, and minimizing unnecessary radiation to surrounding soft tissues and bone.

In one embodiment, the history of the motion of the target can be used by the fluoroscopic image registration system to more precisely predict its location. In one embodiment, the previous motion recorded by the fluoroscopic registration engine is modeled as a 3D path, and the path is mapped to motion tracked according to the fluoroscopic images. In one embodiment, as trends are detected by the fluoroscopic registration engine in the adjustment of target paths, future adjustments are prospectively applied to the target tracking model, enabling dynamic correction of 3D motion paths from the 2D fluoroscopic images by the core registration engine. With periodic motion adjustment based on fluoroscopic registration results of the present invention, these treatment margins can be adjusted—i.e., shrunk, sparing healthy tissue.

In one embodiment, by utilizing the fluoroscopic image registration system technology, the location of a pulmonary lesion in the breathing cycle can be refined to allow treatment radiation beams to be modulated, delivering a radiation dose only when the target is known to be traveling on one of the target paths. In one embodiment, with tighter margins, less dose is delivered to healthy tissue, reducing complications and improving outcomes.

Thus, has been outlined, some features consistent with the present invention in order that the detailed description thereof that follows may be better understood, and in order that the present contribution to the art may be better appreciated. There are, of course, additional features consistent with the present invention that will be described below, and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

The description of the drawings includes exemplary embodiments of the disclosure and are not to be considered as limiting in scope.

DESCRIPTION OF THE INVENTION

Figure 1:
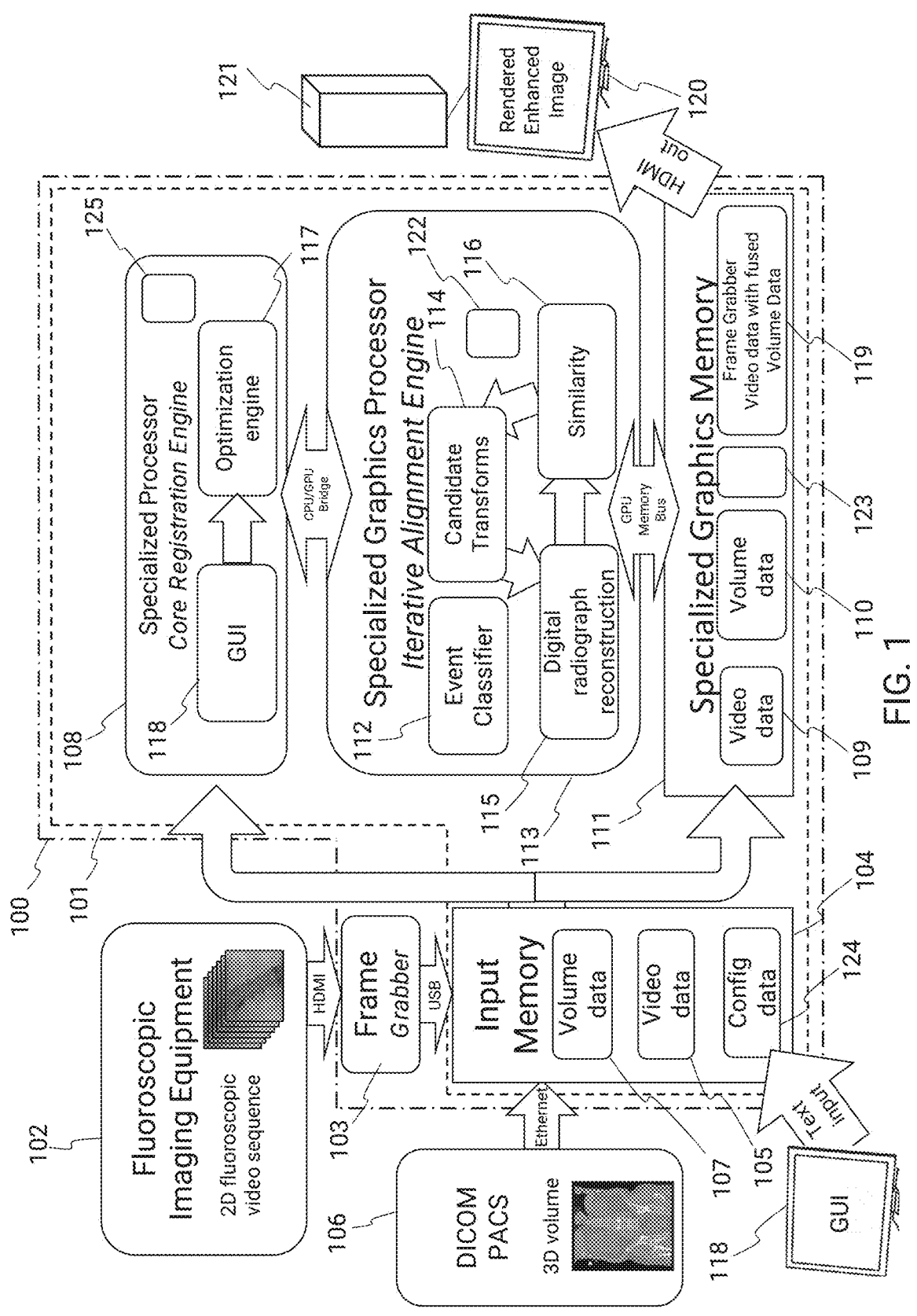
FIG. 1 is a schematic diagram of the fluoroscopic image registration system including its specialized computer resources, according to one embodiment consistent with the present invention.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "includes", "comprises" and/or "including", "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention relates. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that many techniques and steps are disclosed. Each of these has individual benefit and each can also be used in conjunction with one or more, or in some cases all, of the other disclosed techniques, and the steps may be taken in a different sequence than disclosed. Accordingly, for the sake of clarity, this description will refrain from repeating every possible combination of the individual steps in an unnecessary fashion. Nevertheless, the specification should be read with the understanding that such combinations are entirely within the scope of the invention.

Medical applications may be implemented using a system which interfaces with existing information systems such as a Hospital Information System (HIS), a Radiology Information System (RIS), a radiographic device, and/or other information systems such as a Picture Archiving and Communication System (PACS), and/or other systems. The system may be designed to conform with the relevant standards such as Digital Imaging and Communications in Medicine (DICOM). Bi-directional communication between the systems and the information systems, may be enabled to allow the system to retrieve and/or provide information from/to these systems, to update information that is stored on the information systems, and generate desired reports and/or other information.

Fluoroscopic image fusion devices, apparatuses, and methods for aligning and blending non-fluoroscopic images are discussed herein. In the following description, for purposes of explanation, numerous specific details are set forth in order to provide a thorough understanding of the present invention. It will be evident, however, to one skilled in the art that the present invention may be practiced without these specific details, and specific details not disclosed are not meant to be purposefully omitted, but rather, are considered to be well-known in the art.

The fluoroscopic registration system of the present invention may include a client computer such as a personal computer (PC), which may or may not be interfaced or integrated with the PACS, may include an imaging display device that is capable of providing high resolution digital images in 2-D or 3-D, for example. According to one embodiment of the invention, the client computer may be a mobile terminal if the image resolution is sufficiently high. Mobile terminals may include mobile computing devices, a mobile data organizer (PDA), tablet, smart phone, or other mobile terminals that are operated by the user accessing the program remotely.

An input device or other selection device may be provided to select hot clickable icons, selection buttons, and/or other selectors that may be displayed in a user interface using a menu, a dialog box, a roll-down window, or other user interface. The user interface may be displayed on the client computer, or users may input commands to a user interface through a (multi-functional) programmable stylus, key-board, mouse, speech processing device, laser pointer, touch screen, or other input device. The input or other selection device may be implemented by a dedicated piece of hard-ware or its functions may be executed by code instructions that are executed on the client processor. For example, the input or other selection device may be implemented using the imaging display device to display the selection window with a stylus or keyboard for entering a selection.

The client computer may include a processor (internal or external) that includes a central processing unit (CPU) or a graphics processing unit (GPU), a parallel processor, an input/output (I/O) interface, a memory with a program having a data structure, and/or other components, the com-ponents of which may be specialized to perform certain functions which are executed by the program. The client computer may include the input device, the image display device, and one or more secondary storage devices.

The image display device may clearly, easily and accu-rately display images, such as x-rays, and/or other images, and may be implemented using other touch sensitive devices including tablet personal computers, pocket personal com-puters, plasma screens, among other touch sensitive devices. High resolution goggles may be used as a graphical display to provide end users with the ability to review images.

The client computer may include an application that resides on the client computer and written to run on existing computer operating systems or specialized systems. Users may interact with the application through a graphical user interface. The client application may be ported to other personal computer (PC) software, personal digital assistants (PDAs), cell phones, and/or any other digital device that includes a graphical user interface and appropriate storage capability.

The processor may execute a program that is configured to perform predetermined operations. According to one embodiment of the invention, the processor may access the memory in which may be stored at least one sequence of code instructions that may include the program and the data structure for performing predetermined operations. The memory and the program may be located within the client computer or external thereto. While the system of the present invention may be described as performing certain functions, one of ordinary skill in the art will readily understand that the program may perform the function rather than the entity of the system itself.

The program may include separate programs having code that performs desired operations and may include a plurality of specialized modules that perform sub-operations of an operation or may be part of a single module of a larger program that provides the operation. The processor may be adapted to access and/or execute a plurality of programs that correspond to a plurality of operations, such as supporting the user interface, providing communication capabilities, performing data mining functions, performing e-mail opera-tions, and/or performing other operations.

The data storage device may include a database, such as a centralized database and/or a distributed database that are connected via a network and may be relational databases. The data storage device may be coupled to the server and/or the client computer, either directly or indirectly through a communication network, such as a LAN, WAN, and/or other networks or the internet. The data storage device may be an internal storage device or an external storage device.

The client computer may be coupled to other client computers or servers, accessed via a communication link which may include a wired and/or wireless communication link, a switched circuit communication link, or may include a network of data processing devices such as a LAN, WAN, the internet, or combinations thereof. The communication link may couple e-mail systems, fax systems, telephone systems, wireless communications systems such as pagers and cell phones, wireless PDA's and other communication systems, and may be implemented using a specialized piece of hardware or may be implemented using a general CPU that executes instructions from program. According to one embodiment of the invention, the communication link may be at least partially included in the processor that executes instructions from program.

The server is provided in a centralized environment and may be similar in structure and operation to the client computer. Alternatively, a distributed client computer may be provided that includes a plurality of individual proces-sors, which may be located on one or more machines. The server may include a single unit or may include a distributed system having a plurality of servers or data processing units. The server(s) may be shared by multiple users in direct or indirect connection to each other. The server(s) may be coupled to a communication link that is preferably adapted to communicate with a plurality of client computers.

The invention may be implemented using software appli-cations that reside in a client and/or server environment or using software applications that reside in a distributed system over a computerized network and across a number of client computer systems. Thus, a particular operation may be performed either at the client computer, or the server, or both. Operations consistent with the invention may be carried out at the client computer, at the server, or both. The server, if used, may be accessible by the client computer over the Internet.

User interfaces, including graphical user interfaces (GUIs), may be provided that support several interfaces including display screens, voice recognition systems, speak-ers, microphones, input buttons, and/or other interfaces.

Although the above physical architecture has been described as client-side or server-side components, one of ordinary skill in the art will appreciate that the components of the physical architecture may be located in either client or server, or in a distributed environment. Further, although the above-described features and processing operations may be realized by dedicated hardware or may be realized as programs having code instructions that are executed on data processing units, it is further possible that parts of the above sequence of operations may be carried out in hardware, whereas other of the above processing operations may be carried out using software.

The underlying technology allows for replication to various other sites. Each new site may maintain communication with its neighbors so that in the event of a catastrophic failure, one or more servers may continue to keep the applications running, and allow the system to load-balance the application geographically as required.

Further, although aspects of one implementation of the invention are described as being stored in memory, one of ordinary skill in the art will appreciate that all or part of the invention may be stored on or read from other computer-readable media, such as secondary storage devices, like CD-ROM, hard drives, flash drives, or other forms of ROM or RAM either currently known or later developed. Further, although specific components of the system have been described, one skilled in the art will appreciate that the system suitable for use with the methods and systems of the present invention may contain additional or different components.

The present disclosure is to be considered as an exemplification of the invention and is not intended to limit the invention to the specific embodiments illustrated by the figures or description below.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by this disclosure.

In one embodiment, the present invention relates to novel image fusion of three-dimensional (3D) diagnostic images with navigational two-dimensional (2D) images, including for example, 2D x-ray images. More particularly, in one embodiment, the present invention relates to a device and a method that is capable of correcting and fusing previously acquired 3D images and combining them with contemporaneously obtained (live/real-time) 2D images from a device that produces 2D images such as an x-ray fluoroscopic system. This allows a structure such as the abdominal aorta, for example, which might be invisible on a conventional 2D fluoroscopic image to be easily seen and dynamically tracked due to an overlay of that aorta from a CT, MRI, 3D or volumetric ultrasound, or other cross sectional/3D imaging scan.

In one embodiment, the present invention includes a device for transforming a 3D image data set such that the transformed image aligns with a 2D fluoroscopic image data set during a fusion session. The process of the present invention, in finding the transform that aligns the projected features of the 3D image with the 2D image is deemed "image registration" by the inventors.

More particularly, in one embodiment, for the single fusion session, there is a single floating (or moving) image, which will be the image that will be transformed and fused onto every subsequent image loaded in the session under the fluoroscopic registration process. These subsequent images are called reference (or fixed) images, and each time a new reference image is loaded, the floating image for that session is transformed to align with the reference image.

In one embodiment, the present invention relates to multiple stages of finding an optimal set of transformational parameters to drive the match of a digitally reconstructed radiograph (DRR) with the fluoroscopic image, which the inventors have termed as "fluoroscopic image registration".

More specifically, the fluoroscopic image registration system of the present invention has at its core a multistage framework that progressively refines a registration result. In one embodiment, each stage leverages the same core registration engine or module which iteratively searches the parameter space defined by the stage. In one embodiment, the core registration engine creates a candidate transform, uses it to create a digitally reconstructed radiograph (DRR), then compares that to the supplied fluoroscopic image, and then either ends, or uses it to construct a new candidate transform. In one embodiment, similarity measurement of a candidate transform is based on intensities and any custom data relevant to the registration scenario.

In one embodiment, the present invention utilizes a computer with specialized processors, which provide an improvement in the underlying working of the computer and make advancements in the field of medical technology as described further herein.

Figure 2:
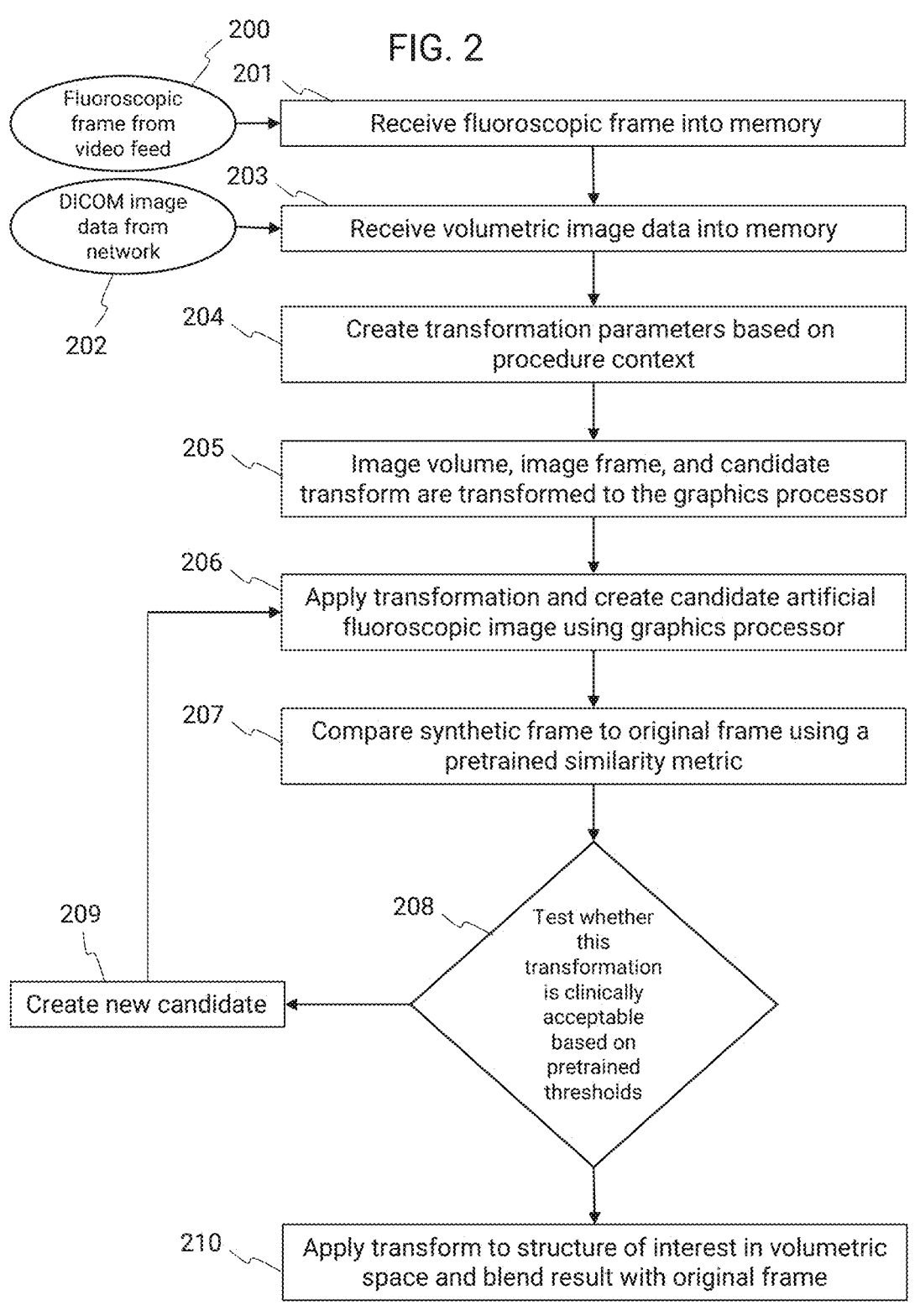
FIG. 2 is fluoroscopic image registration flow chart, used in an example workflow, for overlaying a segmented aorta with a live fluoroscopic image, according to one embodiment consistent with the present invention

In one embodiment of the present invention, FIGS. 1-2 overall show the specialized computer resources and a flow chart of the algorithm and its discrete method steps, as the data from video sources 102 and network sources 106 enter the memory 104 of the fluoroscopic image registration system 100 of the present invention, and undergo processing though the optimization engine or module 117, and the graphics engine or module 113, and is finally rendered back to a display 120.

More specifically, in one embodiment, the fluoroscopic image registration system 100 of the present invention includes a fluoroscopic registration engine 101 or processing board 101, and a separate electronics frame grabber module 103, as shown in FIG. 1. In one embodiment, the fluoroscopic registration engine (FRE) 101 is a three (3) to N degrees-of-freedom (DOF), intensity-based, iterative registration of a fluoroscopic image with a DRR, where the DOF of the FRE spans transformation types from 2D linear in-plane transformations (3 DOF) to 3D linear (6 DOF), to the arbitrary number of dimensions needed to model non-rigid deformation (N DOF). In one embodiment, the fluoroscopic registration engine 101 is located on a client or server or may be a distributed system.

In one embodiment, as shown in FIG. 1, fluoroscopic imaging equipment 102—which includes an X-ray source and a fluorescent screen between which a patient is placed in medical imaging—uses X-rays to obtain real-time moving images of an interior of the patient at a hospital or medical facility. The fluoroscopic imaging equipment 101 can also use other equipment such as X-ray image intensifiers and cameras to improve image visibility, as well as computers that provide image analysis software, data storage and retrieval, and make the images available on a display screen.

In one embodiment, the frame grabber module 103 of the fluoroscopic image registration system 100 is installed either with or separately from the fluoroscopic imaging equipment 102 and connected to same by an HDMI cable, for example. In one embodiment, the frame grabber 103 captures individual, digital still frames from the digital video stream from the fluoroscopic imaging equipment 102 (see FIG. 2, step 200). In one embodiment, the frame grabber module 103 transmits the information on each of the individual digital still frames over a network or cable to an input memory module 104 (step 201, FIG. 2) of the fluoroscopic registration engine 101, where it is stored as video data storage 105.

In one embodiment, a PACS 106 which communicates images via the DICOM standard, which handles the storing and transmitting and medical images at a hospital or medical facility, and which is integrated with medical imaging devices such as scanners, servers, workstations, printers, network hardware, and networks, receives 2D volumetric data from the fluoroscopic imaging equipment 102. In one embodiment, the fluoroscopic registration engine 101 of the present invention collects 3D volumetric data transmitted from the PACS 106 (see step 202, FIG. 2) over a network or cable, and stores the volumetric image data into the input memory module 104 (step 203, FIG. 2) and the volume data storage 107.

In one embodiment, the specialized core registration engine or module 108 of the fluoroscopic registration engine 101 of the present invention includes at least one specialized processor 108 (see FIG. 1) with memory 123, the specialized processor 108 that controls the acquisition of data by the frame grabber module 103 and the PACS 106, and its transmission and storage in the input memory module 104. The core registration engine 108 processes the received data from the video data storage 105 and volume data storage 107 and stores the data in the video data storage 109 and the volume data storage 110, respectively, of the specialized graphic s processor memory module 111 of the fluoroscopic registration engine 101.

In one embodiment, the fluoroscopic registration engine 108 includes at least one specialized graphics processor 113 as the iterative alignment engine 109 (see FIG. 1). In one embodiment, the iterative alignment engine 113 includes an event classifier 112, a candidate transform module 114, a digital radiograph reconstruction module 115, and a similarity module 116.

In one embodiment, the event classifier 112 (see FIG. 1) is used to autonomously determine what registration scenario the fluoroscopic registration engine 101 should be in. In one embodiment, this classification is based on the fluoroscopic video data 105 alone, but does use more than one frame to make that determination. In one embodiment, the event classifier 112 takes as inputs the frames grabbed or taken directly from the fluoroscope 102 by frame grabber 103, and each of the latest frames are transferred by the core registration engine 108 and stored in video data storage 105 of input memory module 104 and transmitted to video data storage 110 of the specialized graphics processor memory module 111 where previous frames are stored as well. In one embodiment, the core registration engine 113 examines the properties of the current image frame (and of the last frame) to dynamically invoke image fusion to create a seamless, interaction-free fusion experience for the user.

Figure 3:
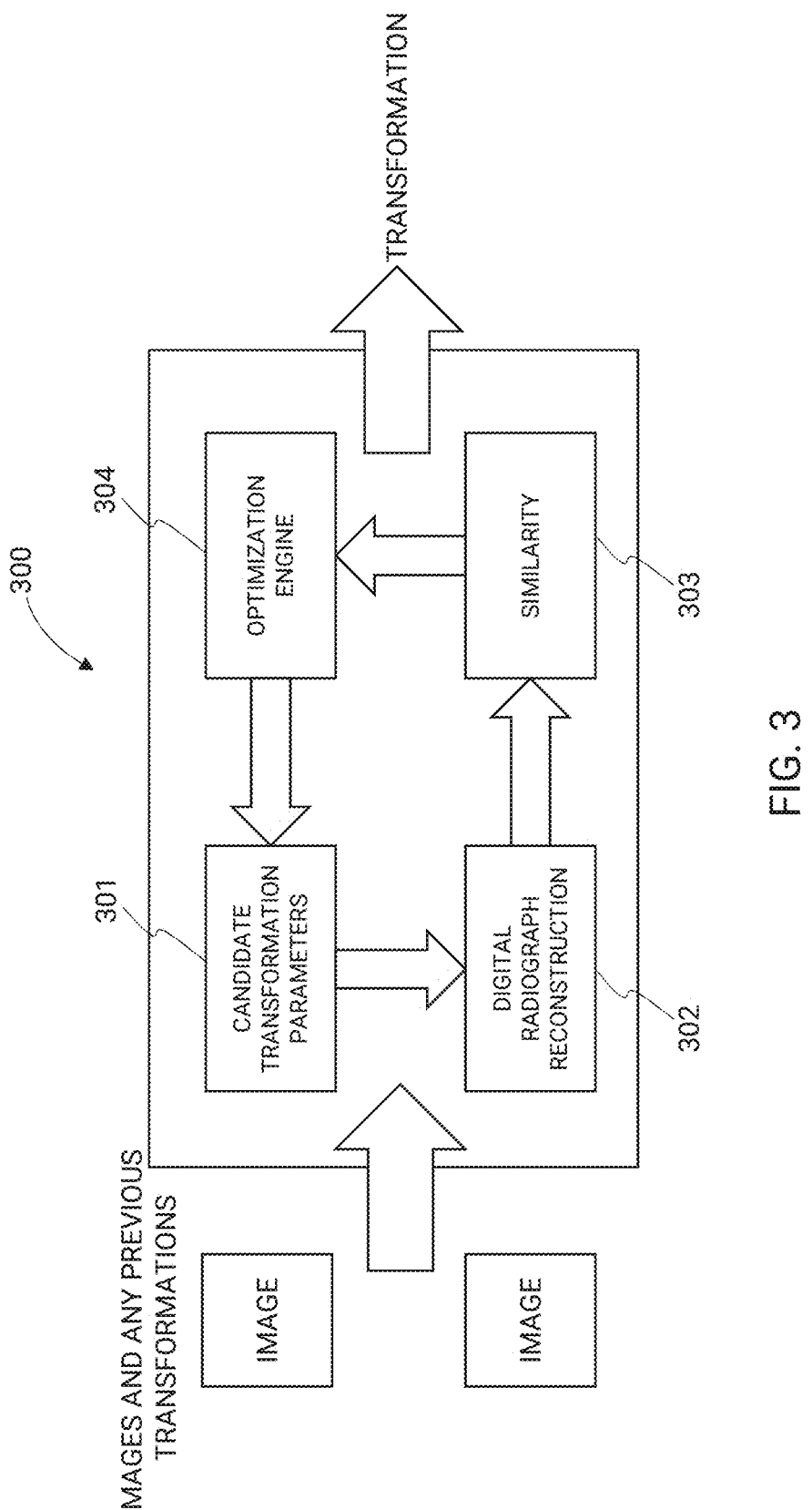
FIG. 3 is a schematic diagram showing the various stages of the fusion process of the fluoroscopic image registration system, according to one embodiment consistent with the present invention.

In one embodiment, the fluoroscopic registration engine 101 is divided into a series of stages 300 shown in FIG. 3. Generally speaking, in one embodiment, the algorithm of the present invention (see FIGS. 1-4B) begins in the first stage by the core registration engine 108 using starting parameters (i.e., images and any previously transformed images) defined by the user position initialization (e.g., anteroposterior (AP) abdomen) and using it to construct a candidate DRR ("candidate transformation parameters" 301) (step 204, FIG. 2). However, many of the functions to achieve same are contributed by the event classifier 112 of the iterative alignment engine 113 (see FIG. 1).

In one embodiment, the similarity of the DRR and actual fluoroscopic image is recorded in memory 125 by the core registration engine 108, and image volume, image frame, and candidate transform are transferred to the iterative alignment engine 113 (step 205, FIG. 2), and the algorithm proceeds iteratively with a perturbed candidate transform in the second stage as controlled by the iterative alignment engine 113 ("digital radiograph reconstruction" 302).

In one embodiment, the resulting similarities determined by the iterative alignment engine 113 (third stage, "similarity" 303), continue to be recorded with an optimization engine 117 of the core registration engine 108, the optimization engine 117 which, in the fourth stage, guides the creation of new candidate transforms from these results ("optimization engine" 304), which are in turn used to generate a DRR image which is then assessed for a match with the latest fluoroscopic navigational image (step 206, FIG. 2).

In one embodiment, in the event that the transformation is not acceptable based on predetermined parameters by the iterative alignment engine 113 (step 208, FIG. 2), a new candidate transform is created (step 209, FIG. 2) by the iterative alignment engine 113. Iterations continue as controlled by the iterative alignment engine 113, until a convergence criterion is reached, and the best candidate transform is applied to a structure of interest in the volumetric space and the result blended with the original fluoroscopic frame (step 210, FIG. 2).

Figure 4A:
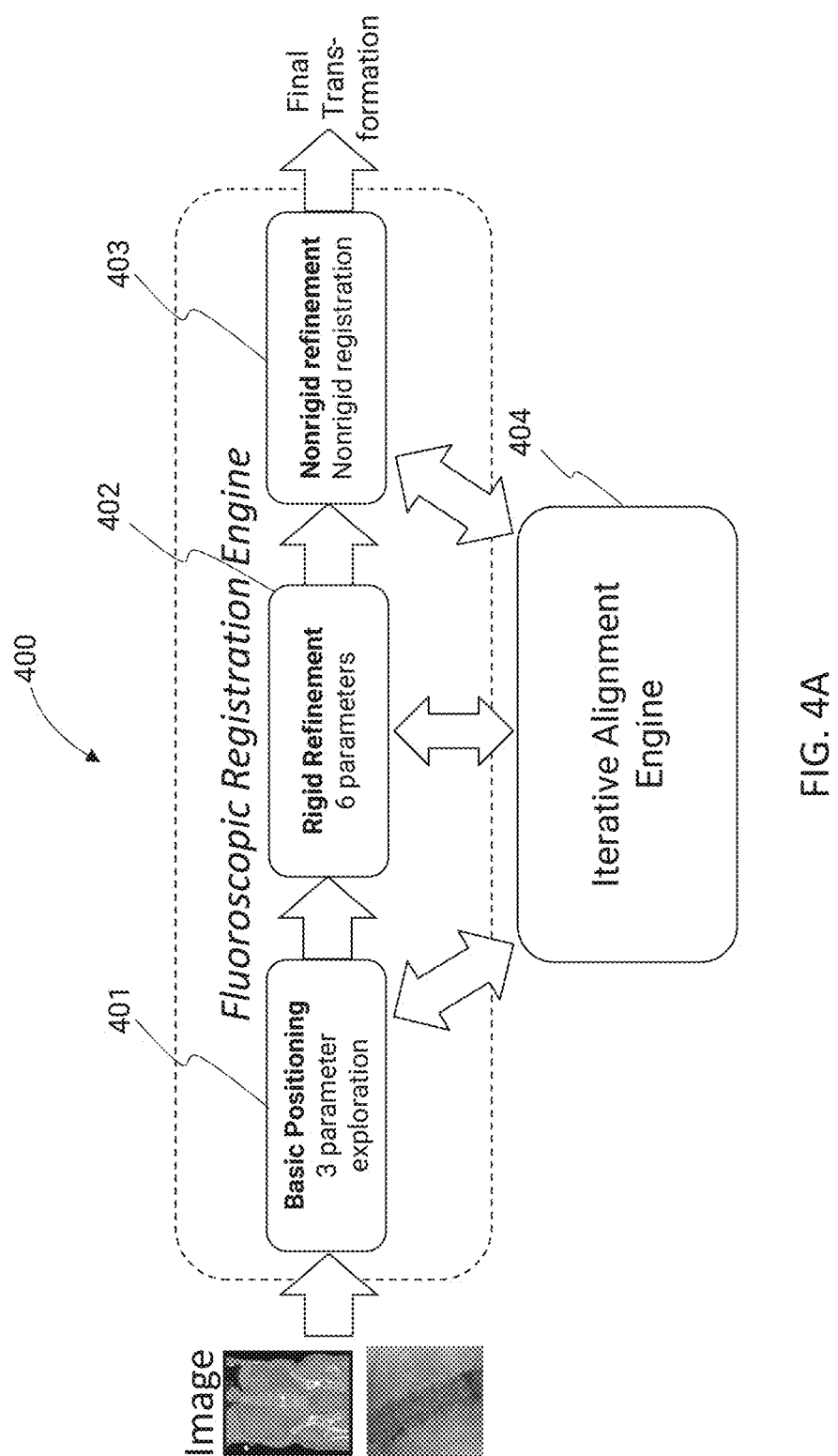
FIG. 4A is a schematic diagram of the registration process of the fluoroscopic image registration system, according to one embodiment consistent with the present invention.
Figure 4B:
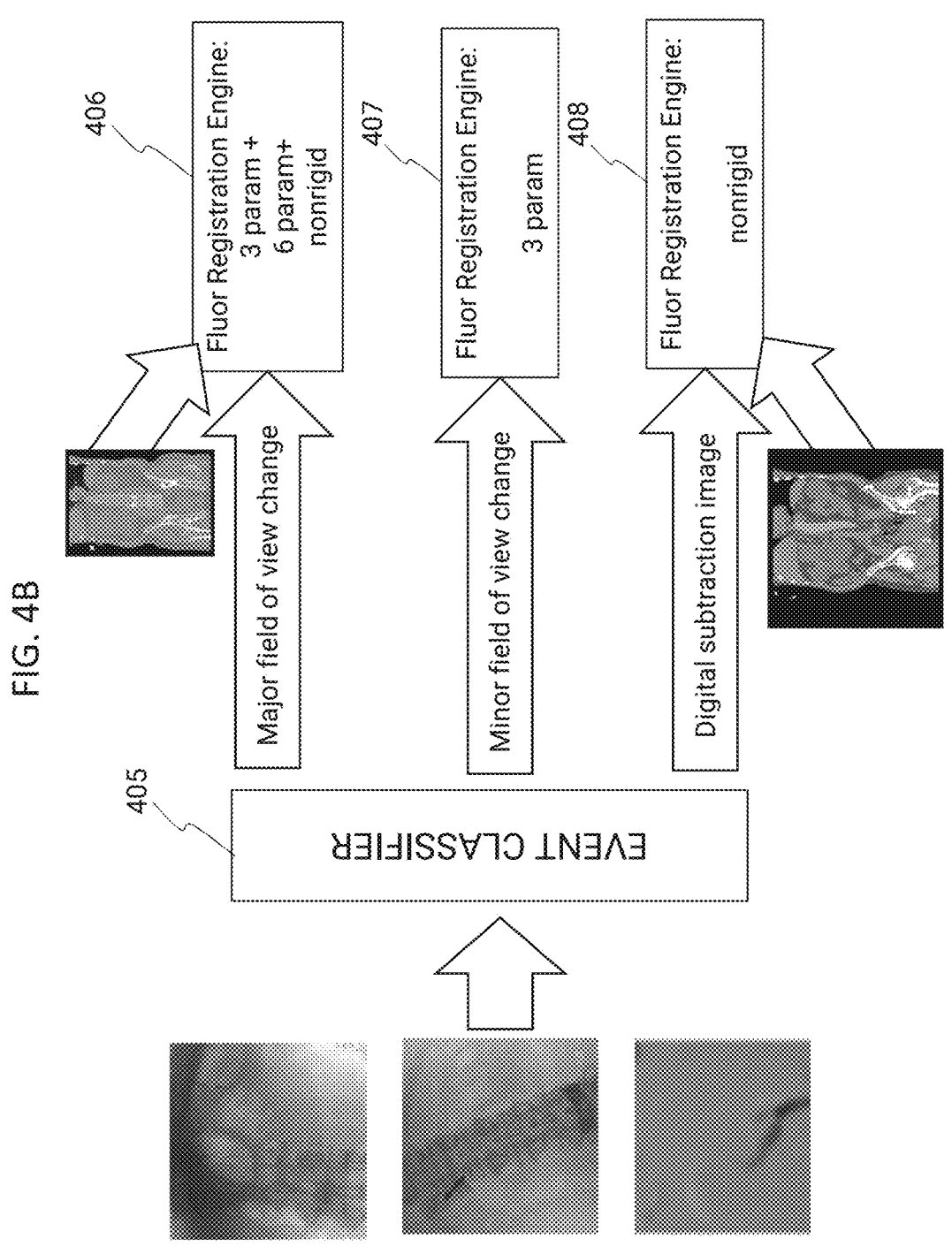
FIG. 4B is a schematic diagram of the registration process of the fluoroscopic image registration system, according to one embodiment consistent with the present invention.

More particularly with respect to creating the candidate transform parameters in the first stage 301/400 (see FIG. 4A), a 3-parameter exploration, rigid refinement with 6-parameters, and nonrigid refinement leading to final transformation of the image is shown in FIGS. 4A-4B. In one embodiment, parameter exploration is iterative and intensity-based for 3-parameter, 6-parameter, and nonrigid refinements.

In one embodiment, with respect to the first stage, the core registration engine 108 creates DRRs of the imaged portion of the body within a field-of-view at the approximate angle and zoom of the fluoroscopic image capture. In one embodiment, the core registration engine 108 configures the novel graphics processor-based implementation of a simplex-based hill-climbing approach (i.e., the iterative alignment engine 113) where a set of candidate solutions form a polyhedron in n-dimensional space. Simplex performs well in the presence of noise that is found in real world clinical images.

In one embodiment, the core registration engine 108 then stitches the DRRs together to create a full body DRR that is then searched by a 3-parameter registration by the core registration engine 108 (see FIG. 4A, "basic positioning, 3-parameter exploration" 401). These three parameters represent a 2D rigid transform (in-plane rotation and in-plane [x-y] translation). In one embodiment, once a matching position is found by the core registration engine 108, the DRR parameters are updated by the core registration engine 108 with this location.

While this step of the present invention creates a coarse overlay of the CT with the DRR, it does not account for out-of-plane rotations or any variation in distance of the body to the camera. In one embodiment of the present invention, to address these misalignments, a 6-parameter registration is performed by the core registration engine 108 based on the starting point from the previous step (see "rigid refinement, 6 parameters" 402).

Since a rigidly registered result does not account for nonlinear motion of structures in the image, such as soft tissue which may stretch and deform from the subject being in a different position or a different stage of breathing, nonrigid registration, in one embodiment of the present invention, addresses these deformations by the core registration engine 108 creating instead of 6-parameter registration, a many-parameter registration in which each parameter can model a local deformation (see "nonrigid refinement, nonrigid registration" 403). In one embodiment, these many parameters coordinate to define an entire deformation field in which each voxel in the volume to be transformed has a unique vector defining where it belongs in the new image. In one embodiment, while a variety of 3D transformation models exist (e.g., uniform grids connected by b-splines, nonuniform grids connected by splines, hierarchical subvolumes connected by quaternion interpolation, etc.), this phase 403 still retains the same basic structure of the previous registration phases 401, 402, in which candidate transforms are created and evaluated iteratively by iteration alignment engine 404.

In one embodiment, as shown in FIG. 3, the fluoroscopic registration engine 101 evaluates DRR images for each match with similarity to determine whether the transformation is clinically acceptable based on pretrained thresholds (step 208, FIG. 2). In one embodiment, the end result of the stages 301-304 is a transformation field that deforms the features within the volume to blend and enhance the alignment between the DRR and the fluoroscopic images (step 210, FIG. 2).

In one embodiment, once the space and initial values have been determined in the first stage by the core registration engine 108, the parameters are transferred by the core registration engine 108 to the iterative alignment engine 113/404 (see FIG. 4A). In one embodiment, the iterative alignment engine 404 works for the 3-parameter and 6-parameter registrations, as well as the nonrigid registration, which adds hierarchy to the exploration to keep the individual problem spaces of nonrigid registration in lower dimensions to mitigate complexity. In one embodiment, the iterative alignment engine 404 is common to each of the phases 401, 402, 403 and utilizes a common iterative registration approach. In one embodiment, for each iteration of the iterative alignment engine 404, the current values of each of the points determines the next candidate solution to be evaluated in the space based on a number of heuristics.

More specifically, in one embodiment, the event classifier 112 filters out empty frames in the video data storage 110 of the graphics processor memory module 111 by an entropy operation that occurs in parallel across the multi-threaded processor(s) of the event classifier 112. In one embodiment, the iterative alignment engine 113 sends the remaining real frames to a macro block (MB) operation that matches and estimates the motion of subblocks across the remaining real frames. In one embodiment, the MB operation is implemented by the event classifier 112 across the multithreaded processor(s) of the event classifier 112 and memory module 122 local to each of the multiprocessor(s) 108, 113, which holds a region of the image.

In one embodiment, the event classifier 112 uses previous frames resident in the same local memory 12 to inform the calculation of the MB motion vectors and these results are merged back into the main global memory 123 by the event classifier 112. In one embodiment, the event classifier 112 sends the data results from the memory 123 to a pretrained classifier that runs on the event classifier's 112 multithreaded hardware to provide a determination of whether the motion vectors are diverse enough to initiate either a partial or a full reregistration of the data (step 208, FIG. 2).

In one embodiment, the determination by the iterative alignment engine 113 can fall into three categories: (1) no re-registration required in which there is minimal change to the motion vectors; (2) partial re-registration required in which there is significant change to the motion vectors; or (3) complete re-registration required in which there is little or no common MB s between the frames.

In one embodiment, in the first (1) case, no parameters are determined by the iterative alignment engine 113 to need recalculation. In one embodiment, in the second (2) case, the iterative alignment engine 113 determines that only half of the parameters need to be recalculated, i.e., just those that are in-plane. In one embodiment, by avoiding a full registration on each frame, the classifier of the iterative alignment engine 113 enables a higher frame rate as (1) and (2) have significantly faster commute times than (3).

In one embodiment, the iterative function of the iterative alignment engine 404 generally leads towards maximization of the novel similarity feature of the similarity module 116, replacing points in the polyhedron with better points when they are found.

In one embodiment, the similarity module 116 utilizes mutual information (MI) to examine the common information of intensity values between two sets of pixels. It does not presuppose any a priori correspondence between pixel values which makes it an ideal candidate for matching real to synthetic images in the present invention. In one embodiment, MI was selected as it has been shown to be a robust metric in a variety of registration scenarios where two images are disparate. In one embodiment, MI is used to calculate the similarity between the DRR and fluoroscopic image (see step 207, FIG. 2). Furthermore, in one embodiment, MI ignores structures that are not in common between the two images, meaning it is robust in the presence of tools and contrast enhancing agents.

In one embodiment, the image registration algorithm utilizes the graphics processor's 113 parallel computing capability. In particular, in one embodiment, the calculation of the normalized mutual information (NMI) between the original fixed image (i.e., fluoroscopic image) and the transformed "floating" image (i.e., DRR image), which is a computationally intensive step in the algorithm, was accelerated in a graphic processor 113 kernel.

In one embodiment, while voxels within a subvolume share memory resources within a multiprocessor 113 to optimize the computing resources for the algorithm, voxels in different subvolumes do not, enabling subvolumes to be mapped to different multiprocessors.

In one embodiment, once an optimized set of 6-DOF rigid transformations for all the subvolumes are found by the iterative alignment engine 113, a resampling graphics processor 113 kernel takes these final transforms, interpolates them to derive a smooth transformation field, and applies it to the floating image to produce a final registered image (step 210, FIG. 2). In one embodiment, the 6-DOF rigid transformation of each voxel is estimated by the iterative alignment engine 113 interpolating the transformations of the subvolume centers surrounding the voxel. In one embodiment of the present invention, the independent components of the transformation are interpolated by the iterative alignment engine 113 separately: three translations along the coordinate axes are determined by tri-cubic interpolation, whereas the 3D rotational pose is determined by spherical cubic quaternion interpolation. In one embodiment, the application of the transform, interpolation, and final resampling are independent at the voxel level, permitting the mapping of each voxel to a single thread. In one embodiment, in both of these kernels, the use of thread groups and threads for the implemented algorithm ensures high utilization of the iterative alignment engine 113 for these time-consuming kernels.

In one embodiment, the transformed image is shown on the display 120 of a client computer system 121. In one embodiment, because the screen of the display 120 must have each pixel defined for each refresh, the iterative alignment engine 113 has a dedicated frame buffer 119. In one embodiment, the frame buffer 119 is an area of memory 111 used to hold the frame of data that is continuously being sent to the display 120.

In one embodiment, the frame buffer 119 is the size of the maximum image that can be displayed and may be a separate memory bank on the graphics card (display adapter) or a reserved part of regular memory 111. In one embodiment, when the fusion completes, the transformed image is transferred to this frame buffer 119, and the display 120 displays the rendered enhanced image from the output frame buffer 119 on its screen.

In one embodiment, the core registration engine 108 includes a graphical user interface (GUI) module 118 (see FIG. 1) that allows the user to interact with the fluoroscopic registration system 100 via the display 120 of the client computer system 121. In one embodiment, the GUI 116 displays on a display screen 120, images received from the input memory 104, and those created by the fusion process via the fluoroscopic registration system 100 and forwarded from the specialized graphics processor memory module 111 and output frame buffer module 114. In one embodiment, a fusion session is defined by a single execution of the GUI 116—in other words, from invocation of the GUI 116, to closing the GUI 116.

In one embodiment, the GUI module 118 supports the loading, viewing and interaction of these medical images received from the input memory 104, and those created by the fusion process via the fluoroscopic registration system 100, collects information from a user to set up the fusion process, such as selecting the appropriate image, and indicating when fusion should begin. In one embodiment, the information is collected into a configuration text file 124 and transferred from input memory 104 into the same main memory 111 with the imaging inputs. In one embodiment, the GUI module 118 utilizes the specialized graphics processor 113 to render its elements which are outputted via frame buffer 119.

With respect to the operation of the present invention, as described above, the present invention assists the user (i.e., medical professional) with the visual evaluation, comparison, and merging of information between anatomical and functional images from a patient. The present invention provides additional information to a user's existing workflow for patient evaluation, and a means for comparison of medical imaging data from multiple DICOM conformant imaging modality sources. The present invention allows the display, fluoroscopic registration and fusing of medical images during diagnostic radiology, oncology, radiation therapy planning, interventional radiology, interventional cardiology, and other medical specialties.

In one embodiment, from the client computer system 121, the user launches the graphics user interface (GUI) 118, which creates a new GUI window with no images loaded on the display 120 screen, and the fluoroscopic registration engine 101 launches the network setup, tests the underlying computer platform, and launces internal services that will perform the fluoroscopic registration of the present invention.

In one embodiment, the core registration engine 108 will show at least a status summary, among other interaction buttons for the user on the display 120, and when ready, will indicate by text or color code etc. on the display 120, that the user can begin and start a new session.

In one embodiment, a session creates two processes: a GUI module 118 interface process, and the fluoroscopic registration engine 101 process as described above. In one embodiment, the user interacts with the GUI 118 while it simultaneously monitors for new fluoroscopic images to arrive as determined by the processes of the fluoroscopic image registration system 100 shown in FIGS. 1 and 3, and as discussed above. The present invention is designed to minimize the amount of interaction needed to see the fusion results from the fluoroscopic registration process.

In one exemplary embodiment, prior to the session beginning, two image sources—fluoroscopic imaging equipment 102 and PACS 106—are preconfigured by the core registration engine 108 to send fluoroscopic images to the fluoroscopic registration engine 101 processing board at the client or server. In one embodiment, the core registration engine 108 pushes an image (Image 1—a floating image) from the PACS 106 imaging source, and the GUI module 118 receives the image via frame buffer 119 and automatically displays the image on display 120.

In one embodiment, in the event of a new image, the image frame is received by the client computer system 120 and it is rendered by the frame buffer 119 to the GUI module's 118 main viewing pane/display screen 120. At this point, in one embodiment, the user may perform certain actions, such as altering window levels (raising, lowering, shrinking, growing in size), or accessing the color map (action indicators), as needed for this image, which will be used by the fluoroscopic image registration engine 101 for the rest of the session.

In one embodiment, the core registration engine 108 pushes another image (Image 2— reference image) from a different imaging source such as the fluoroscopic imaging equipment 102, which is received using the GUI module 118 and via frame buffer 119 and displayed on the display screen 120. In one embodiment, when there are two images, the GUI module 118 creates a registration action for these two images, and the fluoroscopic image registration process is initiated by the fluoroscopic image registration system 101 of the present invention, in which Image 1 is treated by the core registration engine 108 as the floating image and Image 2 is treated by the core registration engine 108 as the reference image, as noted above.

In one embodiment, Image 1 is transformed by the core registration engine 108 and iterative alignment engine 113 (with the intention of correcting for any changes found between Image 1 and Image 2), and the iterative alignment engine 113 fuses Image 1 with Image 2 according to the process described above with respect to the fluoroscopic image registration system 100. In one embodiment, after the fluoroscopic registration engine 101 is completed and fusion takes place, the transformed DRR image is sent back to the GUI 118 which in turn renders the latest image via frame buffer 119. Thus, in one embodiment, the user may again interact with the images via the GUI 118 to perform image reading and manipulation, such as zooming, altering window levels, blending (changing transparency of overlaid image), and panning, etc.

In one embodiment, in the event that the image registration needs a minor adjustment, the user can nudge the registration by using the arrow keys on the display 120 or keyboard of the computer system 121, to nudge the overlay by a few pixels in play.

In one embodiment, errors in image registration are reported to an administrator. Further, in one embodiment, in the event that the image registration process needs to be redone because of misalignment or a large change in position, registration can be re-initialized, and the latest frame will be the new anchor image for registration.

In this exemplary embodiment, at some time later, another image is captured (Image 3) from the fluoroscopic imaging equipment image source 102 which is received, rendered via frame buffer 119, and displayed by the client computer 121 display 120. In one embodiment, Image 3 takes the place of Image 2, which has now been discarded by the core registration engine 108 for the session. In one embodiment, the core registration engine 108 and iterative alignment engine 113 transform Image 1 with respect to Image 3, but since the state of window levels, blending level, and zoom etc., are initially based on the fused image display of Image 1 with Image 2, at this point, the user my again interact with the images on the display 120 as needed, to change the display of the fused image.

In one embodiment, any additional images captured in this session by the core registration engine 108 will continue this pattern of replacing the current reference image while keeping the first image pushed in the session as the floating image. In this exemplary embodiment, there are no more images to capture, so the user closes the GUI 118 which returns to the opening screen on the display 120. The fusion session is now over, and in one embodiment, images used in previous sessions may be directly available (or not) for future sessions.

In one embodiment, facilitating the workflow of this exemplary embodiment and the GUI 118 in general is the underlying core registration engine 108 and iterative alignment engine 113 of the fluoroscopic registration engine 101 which transforms the volumetric image with respect to the fluoroscopic image. In one embodiment, the fluoroscopic registration engine 101 is able to directly transform an image of one modality to an image of a different modality. However, in one embodiment, when pervious frames have been received and fused, the fluoroscopic registration engine 101 of the present invention will heuristically attempt to leverage prior registration results to guide the current registration.

In one embodiment, a detailed log is kept by the core registration engine 108 memory 125 of all actions taken by the user.

In one embodiment, the workflow of this exemplary embodiment can vary in a number of ways to support different needs. For instance, in one embodiment, images may be uploaded from USB or CD by loading the DICOM PACS 106 directly through the GUI 118. In another embodiment, there may be a single imaging source generating all the images used for a session, or there may be many in yet another embodiment. In still another embodiment, fusion can be initiated by the user using a button on the GUI 118 instead of automatically implemented.

In one embodiment, an exemplary workflow of a registration of a 3D volume to a fluoroscopic image, when there are no previous registration solutions related to the current registration, is described below. During a fluoroscopic case, a variety of other scenarios may occur, in which a previous registration from that session will have a transformation result that can be leveraged by the present invention for the current registration problem.

In one embodiment, before the stages that involve the fluoroscopy start, all existing 3D images are registered together using nonrigid registration techniques of the core registration engine 108 (as described above), into the space of the 3D CT image to be registered with the fluoroscopic image. In one embodiment, the 3D CT image is used for the base alignment to the fluoroscopic image.

Figure 5:
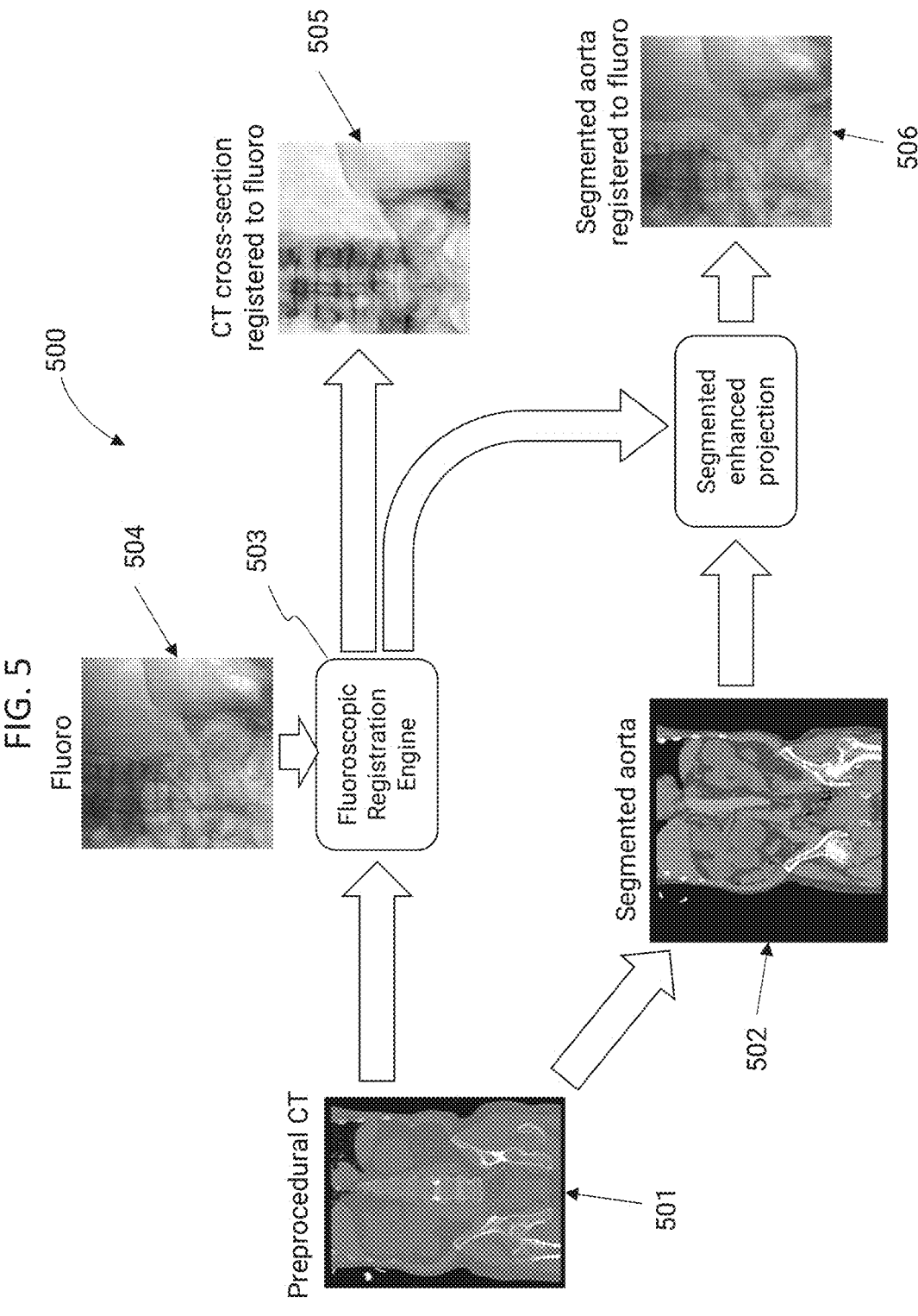
FIG. 5 is a schematic diagram of an exemplary workflow for overlaying a segmented aorta with a live fluoroscopic image, according to one embodiment consistent with the present invention.

More particularly, in one embodiment, this exemplary workflow for the autonomous fusion process of the fluoroscopic registration engine 101, includes using the DICOM PACS 106 push interface in a situation of overlaying a segmented aorta with a live fluoroscopic image (see FIG. 5).

In one embodiment of the exemplary workflow 500, a contrast CT image 501 is first segmented for the aorta 502 (using the appropriate medical tool), which is the vessel of interest in this procedure. In one embodiment, the aorta segment 502 is saved in volume data 110 of the graphics memory 111 by the core registration engine 108, as a label map, creating a new image volume in the same volumetric space as the original CT image 501. In one embodiment, both the aorta segment 502 and the original CT image 501 are pushed by the core registration engine 108 to the image selection process, and the core registration engine 108 selects the images from input memory 104 as the correspondence volume (reference image) and visualization volume (floating image), respectively.

In one embodiment, the abdomen is selected as the location in the body and the initial orientation is selected as AP, by the user. At this point, in one embodiment, the fusion proceeds with the iterative alignment engine 113 of the fluoroscopic registration engine 503 finding a correspondence between the fluoroscopic image 504 and the CT image 501 (see image 505) and using those parameters to overlay the segmented aorta image 502 onto the fluoroscopic image 504 (see overlay image 506), revealing its location in the frame.

In one embodiment, once a mapping is found with the 3D CT image 501 and the fluoroscopic image 504, the other image data that was aligned with the 3D CT image 501 may be used for refinement or enhanced visualization by leveraging the same transformation as described above.

In one embodiment, once the visualization part of the procedure is over, the fluoroscopic image frames are empty on the display 120, prompting the core registration engine 108 to stop the fusion process.

In one exemplary embodiment, some stages of the fluoroscopic registration process can be changed by the fluoroscopic registration engine 101 under the right conditions. For example, once the first visualization image appears, future fluoroscopic images are continually updated with the fusion process of the fluoroscopic image registration system 100. However, an existing common activity of a fluoroscopic camera is to move/translate along the patient to focus on a different area of the body. In one embodiment, imaging tools applied by the user move in the image, but the body remains stationary, so the fusion image remains at the same location.

However, at some point, in one embodiment, a discontinuous pan of the camera frame occurs to a different part of the body due to user action. In one embodiment, the core registration engine 108 detects this and reinitializes the fluoroscopic image registration process, and after a few seconds, a new fusion image is produced by the iterative alignment engine 113. Thus, in one embodiment, the result from a previous image registration process then needs only to be adjusted by the fluoroscopic registration engine 101 by that same translation.

In one embodiment, in the event that the fluoroscopic images overlap (i.e., a smooth pan across the subject with the camera on), then this translation can be uncovered by the fluoroscopic registration engine 101 in the registration of the two registration images. In one embodiment, this translation can be applied to the image being fused to move it as well, providing a fast, accurate update of the image without requiring all registration stages (i.e., similarity, optimization, etc.) to be used.

In another exemplary embodiment with respect to patient position, an angiographic or digital subtraction image, which is commonly acquired when contrast is injected, creates a 2D projection of blood vessels and other structures of the patient. In one embodiment, the enhancement of these structures has not changed the position of the subject, but it has provided new information about the change in shape and position of internal, deformable structures. Similarly, user tools visible in the fluoroscopic image that correspond to structures, such as a catheter introduced into a vessel also inform the deformation of structures. However, in one embodiment, the fluoroscopic registration engine 101 of the present invention updates the corresponding overlay by running the last stage for nonrigid registration and updating only the nonlinear transformations to create a more accurate overlay.

In one embodiment, to invoke each of the above scenarios during a case without requiring additional interaction from the clinician, the event classifier 112 is used in conjunction with the core registration engine 108 as described above. In one embodiment, as noted above, the core registration engine 108 takes as inputs the frames taken directly from the fluoroscope and examines the properties of the current image frame (and of the last frame) to determine which of these scenarios to invoke. In one embodiment, the result is a system that dynamically invokes image fusion to create a seamless, interaction free fusion experience for the user.

Figure 6:
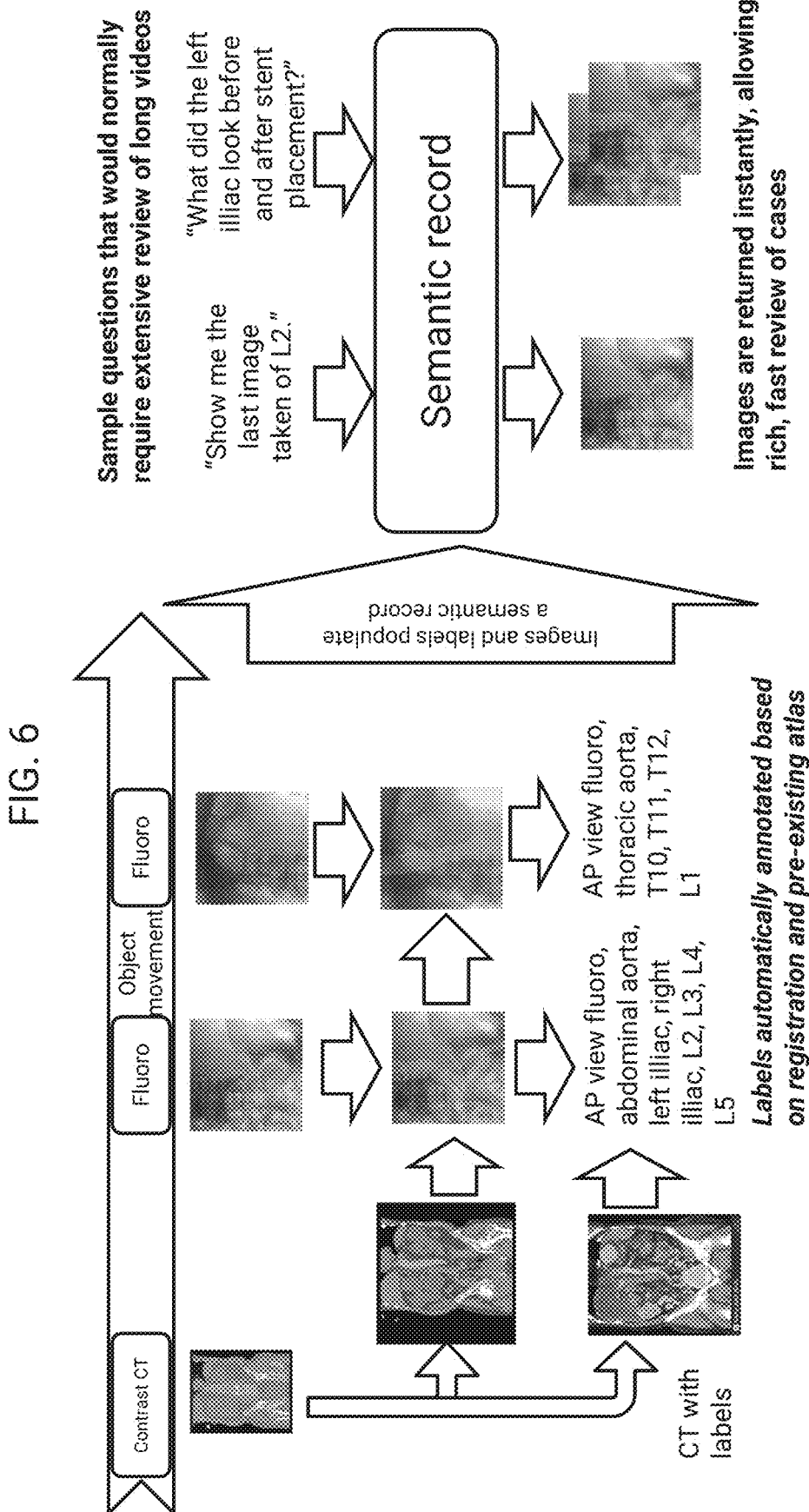
FIG. 6 is a schematic diagram of an exemplary workflow for rich video annotation and indexing, according to one embodiment consistent with the present invention.

In one embodiment, the fluoroscopic registration engine 101 enables a unique method for labeling and indexing fluoroscopic video data, as shown in FIG. 6. In one embodiment, the core registration engine 108 takes the video capture described above with respect to exemplary workflows, and any other annotations created by 3D imaging data (i.e., labels automatically annotated based on registration and pre-existing atlas), and associates the annotation with a set of pixels in each video frame, if present. In one embodiment, this association between 3D labels and 2D video data occurs through the transformation discovered by the fluoroscopic registration engine 101. In one embodiment, with the annotations associated with particular frames, queries by the user (see "sample questions") to the video stream can include these labels, such as anatomy, and are processed by the core registration engine 108 through a semantic process (images and labels populate a semantic record), and which locates from memory 111 and returns images instantly, allowing for rich, fast review of cases.

For example, a clinician in search of a few pertinent frames related to a particular organ can find them all without having to review the entire video sequence, obviating extensive review of long videos. In one embodiment, this method combined with the event classifier 112 labels shown in FIG. 4B further enhances the queries from the user to include labels extracted from the fluoroscopic video sequence itself by the core registration engine 108.

In one embodiment, another use case would be semantic indexing of an interventional procedure using the core registration engine 108 of the fluoroscopic registration engine 101 such that the most important/clinically relevant portions of a procedure can be reviewed, such as stent insertion, or needle biopsy or ablation or contract injection, etc.

Figure 7:
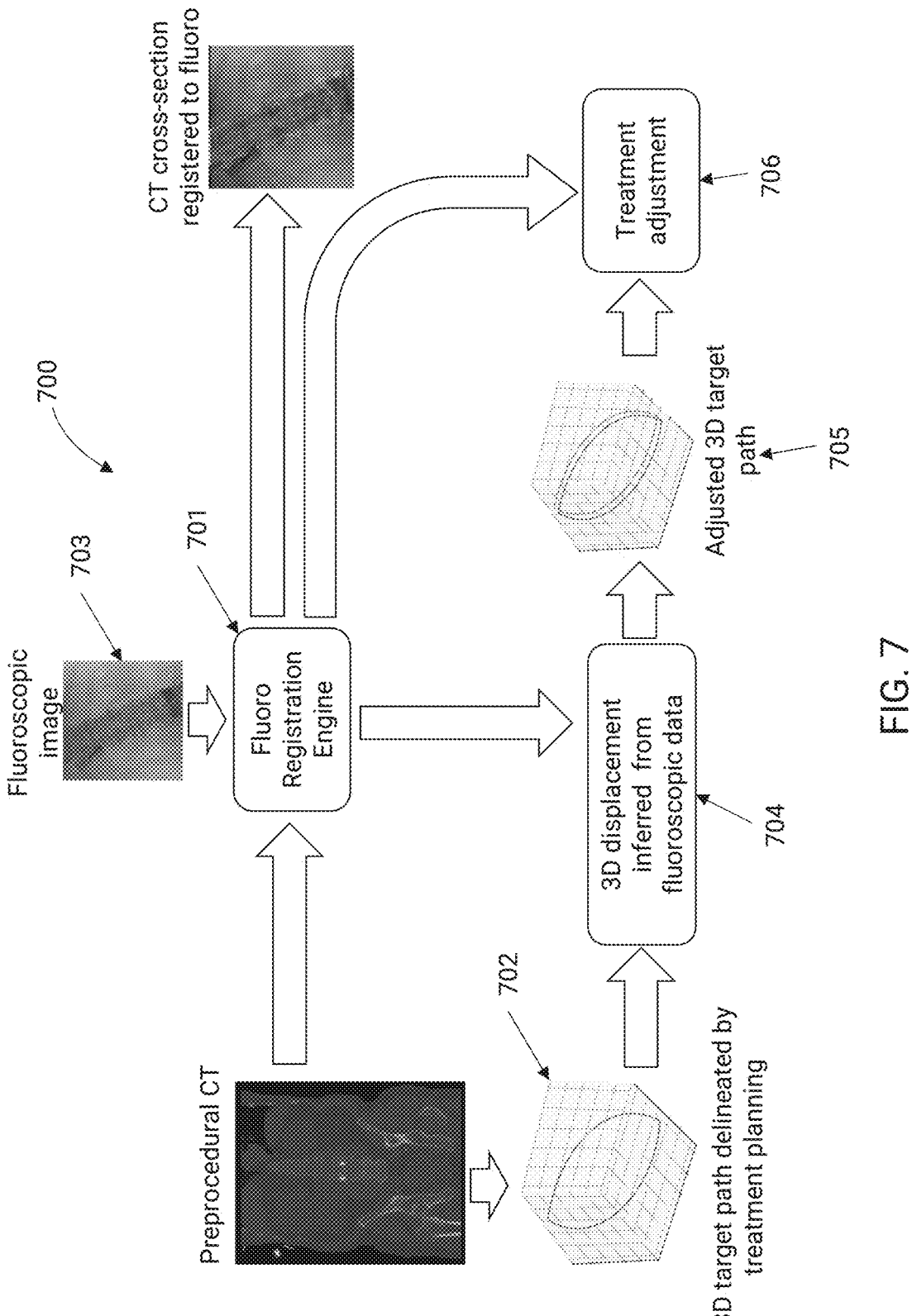
FIG. 7 is a schematic diagram and exemplary process for motion stabilization, according to one embodiment consistent with the present invention.

In another exemplary embodiment, a unique method enabled by the fluoroscopic registration engine 101 is fluoroscopic motion stabilization 700 through target tracking (see FIG. 7). In one embodiment, fluoroscopic stabilization of the present invention fixes a certain object in the same location in a video stream even if it is moving in the raw video feed. For example, spine procedures often utilize conscious sedation, which leads to patient movement during the procedure. With prior art techniques, targeted lumbar vertebrae move during the procedure in the fluoroscopic image along with general patient motion, forcing clinicians to adjust each time. However, with the fluoroscopic registration engine 101 of the present invention, the target can be fixed in a frame, despite actual patient movement, showing only relative movement of surrounding structures.

In another exemplary embodiment, this same method applies in radiation therapy in which a tumor identified on fluoroscopy is fixed as a target location. In one embodiment, patient motion is tracked using the fluoroscopic registration engine 101 and fed back to the treatment delivery system as updated tracking information of actual movement of the tumor. In one embodiment, the target motion captured by the core registration engine 108 is used to guide the radiation beam used to treat the patient, the radiation beam moving along with the tumor, or alternatively, the radiation beam can be modulated or only turned on when the tumor is located within a certain region to maximize the accuracy of the treatment despite patient/tumor motion, and minimizing unnecessary radiation to surrounding soft tissues and bone.

Especially in the case where all degrees of motion cannot be precisely interpreted in real-time, the history of the motion of the target can be used by the fluoroscopic image registration system 100 of the present invention, to more precisely predict its location. In one embodiment, the previous motion recorded by the fluoroscopic registration engine 701 is modeled as a 3D path 702. In one embodiment, this path is mapped to motion tracked according to the fluoroscopic images 703. In one embodiment, image registration creates a bridge between the modeled 3D motion and the 2D movement seen in the fluoroscopic images 703. In one embodiment, a 4-dimensional (4D) image sequence (a periodic time sequenced array of 3D volumes) would be used to create the 3D tracks that model the motion of the target. Conversely, for 3D target motion modeling derived from multiple angles of fluoroscopic images 703, the 2D periodic motions are synchronized, and the target paths triangulated. This can be particularly useful for periodic, repetitive motion such as a beating heart or continuous breathing.

As the periodic motion of a target changes during a session (e.g., due to more labored breathing), in one embodiment, 3D target tracked models are adjusted (see reference numeral 704) by the fluoroscopic registration engine 701. In one embodiment, as trends are detected by the fluoroscopic registration engine 701 in the adjustment of target paths 705, future adjustments are prospectively applied to the target tracking model, enabling dynamic correction of 3D motion paths from the 2D fluoroscopic images by the core registration engine 108.

Periodic motion adjustments have applications in radiotherapy when the target itself is affected by breathing motion. Whether treatment is delivered with fixed beams, motion gated, or with an image guided robot, the current standard of care is to add sufficient margins to the treatment to account for such variation, but that leads to an overtreatment of healthy tissue with harmful radiation. With periodic motion adjustment based on fluoroscopic registration results of the present invention, these treatment margins can be adjusted 706—i.e., shrunk, sparing healthy tissue.

In another exemplary embodiment with respect to pulmonary issues, regarding some of the periodic motion paths of lesions, targets travel in a loop where the initial path of the target is not the same as the return path. For example, in chronic obstructive pulmonary disease (COPD) patients (which is the third most common respiratory diagnosis), patients often have asymmetric paths of motion of targets due to parenchymal lung damage such as can be seen with air blebs or lung refraction associated with scarring. This type of asymmetrical motion complicates current radiotherapy treatment planning, which adds margins to the total area where the target may be. Radiation beam shape and strength is constructed accordingly to ensure that sufficient radiation is delivered to the lesion, but also causes a significant dose of radiation to healthy tissue, leading to complications and worsened patient outcomes.

However, by utilizing the fluoroscopic image registration system 100 technology of the present invention, the location of the lesion in the breathing cycle can be refined as described above with respect to FIG. 6. Just knowing which phase of respiration, the patient is in, can allow, in one embodiment, the treatment radiation beams to be modulated, delivering a radiation dose only when the target is known to be traveling on one of the target paths. In one embodiment, with tighter margins, less dose is delivered to healthy tissue, reducing complications and improving outcomes.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. An image registration system, comprising:
a fluoroscopic registration engine which iteratively refines a digitally reconstructed radiograph (DRR) image from a PACS imaging source, with a fluoroscopic image from a fluoroscopic imaging equipment source, to match said DRR image with said fluoroscopic image, said fluoroscopic registration engine being disposed at one of a client computer or a server;
wherein said fluoroscopic registration engine includes:
a core registration module which creates a candidate transform to achieve said DRR image, and compares said DRR image to said fluoroscopic image;
a graphics memory module including:
a volume data storage that stores volume data from said PACS imaging source;
a video data storage that stores video data from said fluoroscopic imaging equipment source;
wherein said core registration module controls acquisition of said data from said PACS imaging source and said fluoroscopic imaging equipment source, and transmission and storage of said data to said graphics memory module; and
an iterative alignment module which assesses said DRR image for a match with said fluoroscopic image, and proceeds iteratively with a new candidate transform from said core registration module to generate a new DRR image until a match with said new DRR image is achieved, wherein to create the new candidate transform, the core registration module performs 3-parameter registration, which represents a 2D rigid transform on said new DRR image;
wherein the core registration module performs 6-parameter registration after said 3-parameter registration, to account for out-of-plane rotations and any variation in distance of a patient body from fluoroscopic imaging equipment; and
wherein said new candidate transform is applied to a structure in a volumetric space and blended with said fluoroscopic image to result in a transformed image and accomplish image registration.

2. The image registration system of claim 1, further comprising:
an input memory module which receives and stores said data from said PACS imaging source and said fluoroscopic imaging equipment source prior to transmission of said data to said graphics memory module, said input memory module including:
a volume data storage that stores volume data from said PACS imaging source; and
a video data storage that stores video data from said fluoroscopic imaging equipment source.

3. The image registration system of claim 2, further comprising:
a frame grabber module connected to said fluoroscopic imaging equipment source, said frame grabber module which captures individual digital frames from a stream of said video data from said fluoroscopic imaging equipment source, and transmits said video data to said video data storage of said input memory module.

4. The image registration system of claim 3, wherein said core registration module further comprises:
an event classifier which autonomously determines a status of said image registration;
wherein said event classifier takes as inputs a plurality of fluoroscopic image frames grabbed from said fluoroscopic imaging equipment source by said frame grabber module, such that said core registration module examines properties of a current fluoroscopic image frame of said plurality of fluoroscopic image frames to compare with said DRR image to ascertain said match and to dynamically invoke said image registration.

5. The image registration system of claim 4, further comprising:
a display of a computer system; and
wherein said core registration module further comprises:
a graphical user interface (GUI) module that supports loading, viewing and interaction of fluoroscopic images received from said input memory module, and allows a user to interact with the fluoroscopic registration engine and display at least one of said fluoroscopic images and said transformed image on said display screen.

6. The image registration system of claim 5, wherein said graphics memory module further comprises:
an output frame buffer module which receives said transformed image from said iterative alignment module and transfers said transformed image to said display as a rendered image.

7. The image registration system of claim 6, wherein said iterative alignment module further comprises:
a candidate transform module which uses starting parameters of said DRR image and any previously transformed DRR images to construct said new candidate transform;

a digital reconstruction module which takes said new candidate transform and generates said new DRR image; and a similarity module which determines similarities between said new DRR image and said fluoroscopic image to determine said match.

8. The image registration system of claim 7, wherein said core registration module further comprises:

an optimization module which guides a creation of said new candidate transform of said candidate transform module from results of said similarities found by said similarity module.

9. The image registration system of claim 1, wherein nonrigid registration is performed on said new DRR image to account for nonlinear motion of structures, where each parameter of a multi-parameter nonrigid registration can model a local deformation in said new DRR image.

10. A method of performing image registration, comprising:

launching an image registration session on a display of a computer system utilizing a graphics user interface (GUI) module, said GUI module which provides an interface for a user and a fluoroscopic image registration system;

initiating a fluoroscopic registration engine of said fluoroscopic image registration system, said fluoroscopic registration engine being disposed at one of a client computer or a server;

wherein said fluoroscopic image registration engine performs the following steps:

creating a candidate transform using a core registration module of said fluoroscopic registration engine to achieve a digitally reconstructed radiograph (DRR) image;

comparing said DRR image to said fluoroscopic image using an iterative alignment module of said fluoroscopic registration engine;

assessing said DRR image for a match with said fluoroscopic image;

iteratively refining said DRR image with a new candidate transform from said core registration module to generate a new DRR image until a match with said new DRR image is achieved;

wherein to create the new candidate transform, the core registration module performs 3-parameter registration, which represents a 2D rigid transform on said new DRR image; and wherein the core registration module performs 6-parameter registration after said 3-parameter registration, to account for out-of-plane rotations and any variation in distance of a patient body from fluoroscopic imaging equipment;

applying said new candidate transform which achieves said match, to a structure in a volumetric space; and blending said new candidate transform with said fluoroscopic image to result in a transformed image and image registration.

11. The method of performing image registration of claim 10, wherein said core registration module controls acquisition of said data from said PACS imaging source and said fluoroscopic imaging equipment source, and transmission and storage of said data to a graphics memory module.

12. The method of performing image registration of claim 11, further comprising:

capturing individual digital frames from a stream of video data from said fluoroscopic imaging equipment source using a frame grabber module connected to said fluoroscopic imaging equipment source; and transmitting said video data to a video data storage of an input memory module of said fluoroscopic registration engine.

13. The method of performing image registration of claim 12, further comprising:

autonomously determining a status of said image registration using an event classifier of said iterative alignment engine module;

wherein said event classifier takes as inputs a plurality of fluoroscopic image frames grabbed from said fluoroscopic imaging equipment source by said frame grabber, such that said core registration module examines properties of a current fluoroscopic image frame of said plurality of fluoroscopic image frames to compare with said DRR image for said match and to dynamically invoke said image registration.

14. The method of performing image registration of claim 13, further comprising:

providing a display on which at least one of said fluoroscopic images received from said input memory module, and said transformed image received from an output frame buffer module, are displayed such that said user can load, view, and interact with said fluoroscopic images;

wherein said output frame buffer module receives said transformed image from said iterative alignment module and transfers said transformed image to said display as a rendered image.

15. The method of performing image registration of claim 14, further comprising:

constructing said new candidate transform using a candidate transform module of said iterative alignment module, by using starting parameters of said DRR image and any previously transformed DRR images to construct said new candidate transform;

generating said new DRR image using a digital reconstruction module of said iterative alignment engine; and determining similarities between said new DRR image and said fluoroscopic image to determine said match, using a similarities module of said iterative alignment engine.

16. The method of performing image registration of claim 15, further comprising:

creating said new candidate transform of said candidate transform module using an optimization module of said core registration module, from results of said similarities determined by said similarity module.

17. The method of performing image registration of claim 10, further comprising:

performing nonrigid registration on said new DRR image to account for nonlinear motion of structures, where each parameter of a multi-parameter nonrigid registration can model a local deformation in said new DRR image.

* * * * *